United States Patent [19]

Jaeger

[11] Patent Number: 4,866,033

[45] Date of Patent: Sep. 12, 1989

[54] OLIGOPEPTIDES FROM BOVINE BLOOD

[76] Inventor: Karl-Heinrich Jaeger, Matthofstrand 9, Luzern, Switzerland

[21] Appl. No.: 140,169

[22] Filed: Dec. 31, 1987

[30] Foreign Application Priority Data

Dec. 31, 1986 [DE] Fed. Rep. of Germany ....... 3644805

[51] Int. Cl.⁴ .................... A61K 35/14; A61K 37/18
[52] U.S. Cl. .......................................... 514/2; 435/69; 435/269
[58] Field of Search ...................... 435/69, 269; 514/2

[56] References Cited

U.S. PATENT DOCUMENTS 2,912,359  11/1959  Anigstein et al. ................. 435/69

Primary Examiner—Sam Rosen
Attorney, Agent, or Firm—Cushman, Darby & Cushman

[57] ABSTRACT

Oligopeptide mixtures from deproteinized bovine blood dialyzate which are characterized by their RF values in thin-layer chromatography, as well as a method for their preparation.

2 Claims, No Drawings

4,866,033

OLIGOPEPTIDES FROM BOVINE BLOOD

BACKGROUND OF THE INVENTION

The invention relates to oligopeptides extracted from bovine blood and to a method for their preparation and usage.

It has long been known that active substances which increase respiration and activate the metabolism can be prepared from bovine blood. Thus, for example, DE-PS No. 10 76 888 describes a method of extracting such active substances beneficial for respiration from bovine blood. The method involves fractionated deproteinization for removing the high molecular weight constituents, after which the blood is fermentatively degraded or subjected to dialysis with water and alcohols, whereupon the dialysate is subsequently freed of solvent and dried in a protective manner. The concentrates prepared according to this method improve the utilization of oxygen in the human organism and can therefore be used to treat any illness in which an oxygen deficiency is to be eliminated. In the Federal Republic of Germany, bovine blood dialysates are commercially available e.g. from the firms Byk Gulden, Solco and Chemische Werke Linz under the trade names "Actihaemyl", "Solcoseryl" and "Actovegin", which are used to treat peripheral and central circulatory disturbances and the conditions resulting therefrom. However, the problem with these blood dialysates and also with other organic extracts resides in the fact that the composition of such extracts varies a great deal depending on the conditions of the method of preparation. It has been possible in only a few instances up to the present to clarify the composition and structure of such peptides in detail. A clarification of the composition and structure permits standardization and perhaps synthesis of the active compounds. Moreover, because the many individual peptides in the dialysate have different activities and activities of differing intensities, concentration of the most active compounds and standardization are extremely desirable.

The invention therefore has as its object the development of new oligopeptide mixtures from bovine blood dialysates to satisfy the need for such preparations with a reproducible composition.

SUMMARY OF THE INVENTION

The invention achieves its objective by describing the preparation and composition of certain oligopeptide mixtures obtained from deproteinized bovine blood dialysate. The oligopeptide mixture according to the present invention exhibits $R_f$ values of 0.0045, 0.196, 0.245, 0.4, 0.44, 0.52, 0.66 and 0.8 after four hours under thin-layer chromatographic separation on silica gel using a mixture of n-butanol, glacial acetic acid and water in a 4:1:1 ratio as a developing solvent. Detection is accomplished with a 0.1% ninhydrin reagent for 15 minutes at 110° C.

DETAILED DESCRIPTION OF THE INVENTION

The oligopeptides are prepared from the blood of cattle inspected by veterinarians, especially from cattle whose germ count was checked in advance. The bovine blood is diluted by the addition of a threefold amount of germ-free distilled water and a pH is then adjusted to 7.00 with hydrochloric acid or sodium hydroxide solution. The mixture is heated to 40° C., pepsin and papain are added and the mixture is fermented 15 hours at 40° C. In order to inactivate the enzymes, the mixture is then heated to 90° C. and kept at 90° C. for 30 minutes, filtered and then cooled to approximately 20° C. Then a double amount of at least 95 (V/V)% ethanol is added, and the mixture is cooled and stored at least 12 hours. Subsequently, the mixture is concentrated by evaporation and mixed once again with a fourfold amount by weight of 95% ethanol, agitated 5 hours and cooled at least 12 hours. Finally, the mixture is concentrated by evaporation in order to remove the ethanol; the remaining aqueous solution is ultrafiltered through membranes with a separation limit for molecular weights of under 2,000. This ultrafiltrate is then concentrated in a vacuum and dried. The product is a yellow crystalline, hygroscopic powder which exhibits a pH of approximately 6-7 in 1% aqueous solution. The osmolality of the 1% solution is between 0.07-0.08 osm/kg. A solution of this substance yields no precipitation with trichloroacetic acid and sulfosalicylic acid, which indicates that no free amino acids in a demonstrable amount are contained.

The peptide mixture prepared in this manner is identified by thin-layer chromatography, whereby silica gel is used as an adsorbent and a mixture of n-butanol, glacial acetic acid and water in a ratio of 4:1:1 is used as an eluting solvent. The running time is 4 hours and the length of the run is 15 cm of chamber saturation. The detection is performed with a 1% ninhydrin reagent while heating for 15 minutes to 110° C. The amount applied is 0.1 ml. The polypeptide mixture exhibits $R_f$ values in the regions around 0.0045, 0.196, 0.245, 0.4, 0.44, 0.52, 0.66 and 0.8.

The peptide mixture yields on the average the following content of amino acids after 24 hours of hydrolysis (in mmoles/g):

| asparaginic acid | 280 | methionine | 71.0 |
| --- | --- | --- | --- |
| threonine | 270 | isoleucine | 42.5 |
| serine | 300 | leucine | 540 |
| glutaminic acid | 240 | tyrosine | 120 |
| proline | 280 | phenyl alanine | 250 |
| glycine | 340 | ornithine | 15 |
| alanine | 570 | lysine | 285 |
| cystine | 9.0 | histidine | 240 |
| valine | 315 | arginine | 115 |

The product of the invention can also be clearly distinguished chromatographically from the products prepared according to known methods. Free protein liquid chromatography (FPLC) was performed with an apparatus of the firm Pharmacia using HR 5/5 columns, which are particularly suitable for separation in a peptide range up to 5000 Daltons. The product of the invention was chromatographed, along with the commercially available products "Solcoseryl" and "Actihaemyl", which are prepared according to known methods, for purposes of comparison. Each of the preparations was diluted 1:2 with an aqueous buffer. The running conditions were identical for all substances. Phosphate buffered saline (PBS), pH 7.2, was used as the buffer; the flow speed was 1 mm/min. The differences in composition are clearly shown in the graphs attached as FIG. 1.

In the Warburg test, which measures the increase in oxygen consumption of mouse liver homogenate, the oligopeptides of the present invention exhibited an increase of respiration of approximately 250% relative to the reference. This increase is approximately 100 to 150% greater than the values of the preparations previously on the market.

The dried peptide concentrates prepared according to the method described can be further processed in a known manner to produce medicaments for oral or intravenous use. For oral use, coated tablets are produced in a customary manner with the addition of carrier substances and other adjuvants, since a better storage life can be achieved with coated tablets than with other oral preparation forms. However, since the active substances are peptides, the dried concentrates are preferably prepared in the form of injection solutions by further processing of the dried substance in a known manner to produce an aqueous solution. Benzyl alcohol is preferably used as a preservative for injection solutions of this type. The dosage is preferably between approximately 50–200 mg of the active substance mixture.

The peptide mixtures used in accordance with the invention result in an acceleration of metabolic processes independently of the organs as well as in an improvement of the microcirculation. Accordingly, they can be used to treat peripheral and central circulatory disturbances and also to improve the healing of wounds, for example burns or ulcers. The medicament may also be administered to increase the radiotolerance of body cells or to improve acceptance of the edges of skin transplants. The invention is explained in greater detail below with reference to the examples.

1. Preoaration of the peotide mixture 950 l bovine blood was diluted after determination of a germ count of below 23 in a ratio of 1:3 with germ-free distilled water. The pH of the solution was determined and adjusted to pH 7 by the addition of either 1N hydrochloric acid or 1N sodium hydroxide solution. The diluted blood was heated to 40° C. and mixed with 9.4 kg of both pepsin and papain and 0.05% benzyl alcohol for preservation under agitation. After a complete mixing, the pH was readjusted, if necessary. The enzymatic action continued for 15 hours under continuous agitation. Then, the pH was rechecked. In order to inactivate the enzymes, the solution was heated to 90° C. and maintained at this temperature for 30 minutes. The still hot solution was clarified by filtration.

After determining the amount of dry residue, the residue was adjusted either by evaporation or by dilution with germ-free distilled water so that there was 10 l water per 1 kg dry substance. The resulting 800 l solution was agitated for one hour while 1,600 l of at least 95 (V/V) % ethanol was added. The mixture was then agitated for 5 hours at 20° C. The solution was stored overnight in a cold-storage room at 4° C. On the following day, the solution was clarified by filtration under a pressure of 1–1.5 atmospheres above atmospheric pressure.

The alcoholic solution was concentrated by evaporation in a suitable vacuum evaporator at 40° C. to approximately 160 l, then the pH was again adjusted to pH 7. The solution was weighed and mixed within an hour at 20° C. under agitation with 4 parts by weight 95% ethanol and agitated 5 hours more. After a residence time of at least 12 hours in a cold-storage room, the solution was again clarified by filtration under a pressure of 1–15 atmospheres above atmospheric pressure. The alcohol was subsequently drawn off with an evaporator. For the ultrafiltration, the resulting aqueous solution was pressed under pressure through a membrane at the separation limit for a molecular weight of below 2,000. The aqueous solution of the ultrafiltrate was concentrated under a vacuum and dried. The remaining residual moisture was removed from the concentrate in a drying oven.

The extract was a yellowish, crystalline, hygroscopic powder. The yield of ultrafiltered dry substance is approximately 28 kg.

2. Preparation of an injection solution 8,800 kg of the ethanolic extract according to example 1 and 2,200 kg benzyl alcohol were dissolved under agitation in 212,630 kg sterile water for injection purposes. The pH was adjusted to 5.8. Then the mixture was filtered sterile via a cellulose nitrate filter with a pore size of $0.2\mu$ and deposited into sterile ampules under nitrogen and sealed off.

3. Identification of the peptide mixture

Identification was performed by thin-layer chromatography on silica gel 60 manufactured by the Merck Company without a fluorescence indicator, with a mixture of n-butanol, glacial acetic acid and water as an eluting solvent in a ratio of 4:1:1. The running time was 4 hours; the amount applied was 1 ml. Dying was performed using a 0.1% ninhydrin spray reagent, and developed for 15 minutes at 110° C. The developed chromatogram exhibits the following Rf values: 0.0015, 0.196, 0.244, 0.40, 0.44, 0.52, 0.66 and 0.8.

We claim:

1. An oligopeptide mixture from deproteinized bovine blood dialysate, comprising oligopeptides having $R_f$ values of about 0.0045, 0.196, 0.245, 0.40, 0.44, 0.52, 0.66 and 0.8 after 4 hours under a thin-layer chromatographic separation on silica gel using a mixture of n-butanol, glacial acetic acid and water in a ratio of 4:1:1 as a developing solvent.

2. The oligopeptide mixture according to claim 1, further comprising a total amino acid content in mmoles/g of about:

| asparaginic acid | 280 | methionine | 71.0 |
| --- | --- | --- | --- |
| threonine | 270 | isoleucine | 42.5 |
| serine | 300 | leucine | 540 |
| glutaminic acid | 240 | tyrosine | 120 |
| proline | 280 | phenyl alanine | 250 |
| glycine | 340 | ornithine | 15 |
| alanine | 570 | lysine | 285 |
| valine | 315 | histidine | 240 |
| cystine | 9.0 | arginine | 115 |

* * * * *